United States Patent [19]
Watson et al.

[11] Patent Number: 5,543,012
[45] Date of Patent: Aug. 6, 1996

[54] APPARATUS FOR MAKING A STRETCHABLE BAND-TYPE TRANSDUCER PARTICULARLY SUITED FOR USE WITH RESPIRATION MONITORING APPARATUS

[75] Inventors: Herman L. Watson; Chu Pak, both of Miami, Fla.

[73] Assignee: Non-Invasive Monitoring Systems, Inc., Miami Beach, Fla.

[21] Appl. No.: 410,570

[22] Filed: Mar. 24, 1995

Related U.S. Application Data

[62] Division of Ser. No. 912,218, Jul. 10, 1992, abandoned, which is a continuation of Ser. No. 824,752, Jan. 17, 1992, abandoned, which is a continuation of Ser. No. 517,438, May 1, 1990, abandoned, which is a continuation of Ser. No. 316,996, Feb. 28, 1989, abandoned, which is a continuation of Ser. No. 932,724, Nov. 19, 1986, Pat. No. 4,807,640.

[51] Int. Cl.⁶ ............................................ A61B 5/08
[52] U.S. Cl. .................. 156/440; 156/177; 156/179; 156/439; 219/549
[58] Field of Search .................. 156/177, 179, 156/439, 440; 219/549; 128/644, 716, 721, 774, 782, 798, 641; 428/317.5, 209; 340/578

[56] References Cited

U.S. PATENT DOCUMENTS

| | | | |
|---|---|---|---|
| 2,613,306 | 10/1952 | Waltersdorf et al. | 219/549 X |
| 3,573,151 | 3/1971 | Dawbarn | 156/439 X |
| 3,756,893 | 9/1973 | Smith | 156/440 |
| 3,829,339 | 8/1974 | Pinette | 156/179 |
| 3,888,240 | 6/1975 | Reinhold, Jr. et al. | 128/644 |
| 4,257,424 | 3/1981 | Cartmell | 128/641 |
| 4,265,253 | 5/1981 | Abraham | 128/798 |
| 4,308,872 | 1/1982 | Watson et al. | 128/721 X |
| 4,373,534 | 2/1983 | Watson | 128/721 X |
| 4,409,059 | 10/1983 | Holroyd et al. | 156/439 X |
| 4,452,252 | 6/1984 | Sackner | 128/721 X |
| 4,456,015 | 6/1984 | Sackner | 128/721 |
| 4,807,640 | 2/1989 | Watson et al. | 128/721 |
| 4,839,227 | 6/1989 | Hoopman | 428/209 |
| 4,867,166 | 9/1989 | Axelgaard et al. | 128/798 |
| 4,877,470 | 10/1989 | Krueger | 156/177 |
| 4,934,383 | 6/1990 | Glumac | 128/798 |
| 4,971,065 | 11/1990 | Pearce | 128/721 |

FOREIGN PATENT DOCUMENTS

| | | | |
|---|---|---|---|
| 735867 | 6/1966 | Canada | 156/179 |
| 2116725 | 9/1983 | United Kingdom | 128/721 |

*Primary Examiner*—Jeff H. Aftergut
*Attorney, Agent, or Firm*—Cohen, Pontani, Lieberman, Pavane

[57] ABSTRACT

An improved, low-cost stretchable band incorporating a conductor for disposition around the human torso or other three-dimensional object, and particularly intended for use with respiration monitoring apparatus, is disclosed. Also presented is an improved enclosure housing circuitry releasable connected to the conductor in the band when the band is incorporated in respiration monitoring apparatus.

6 Claims, 9 Drawing Sheets

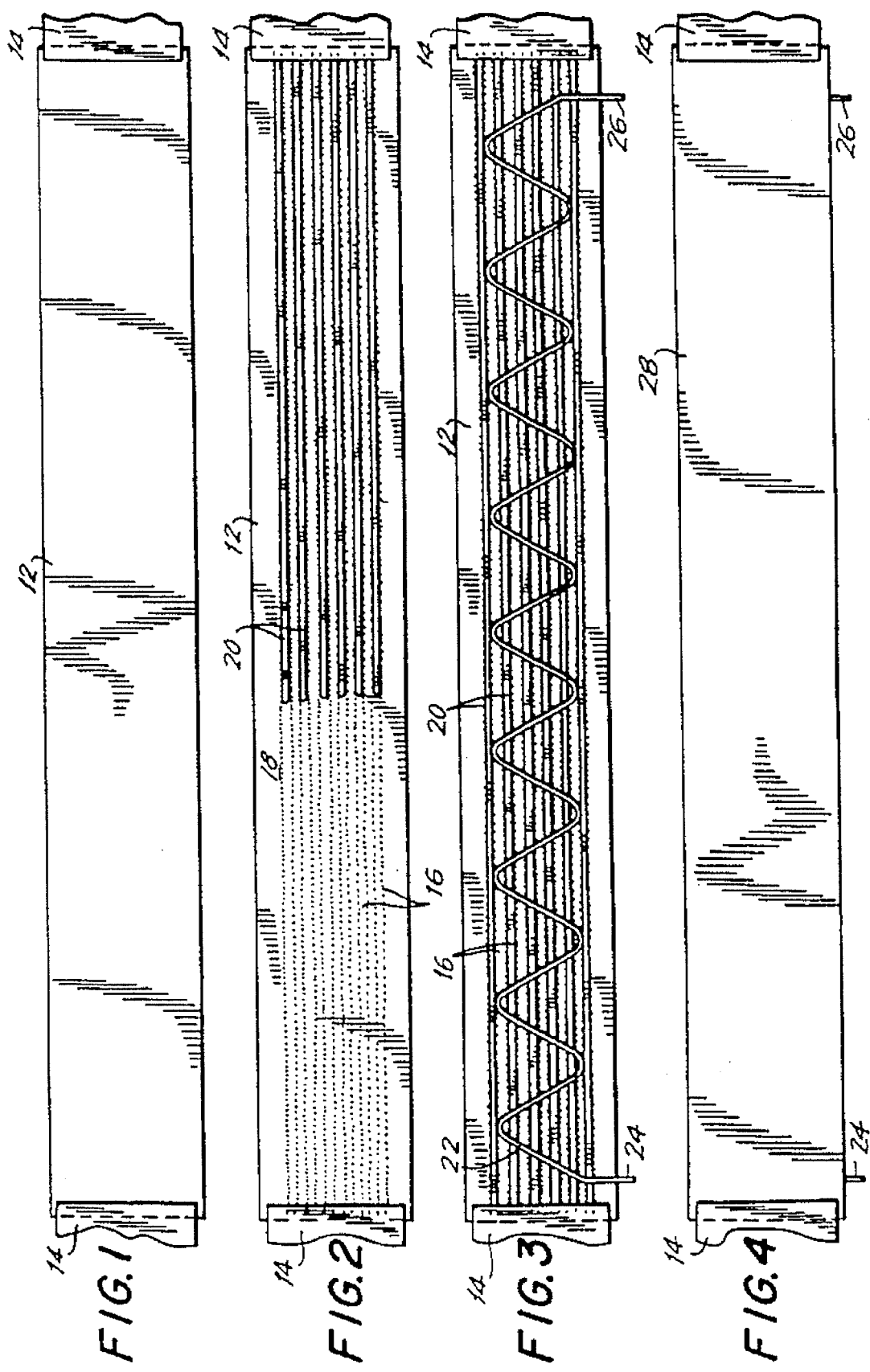

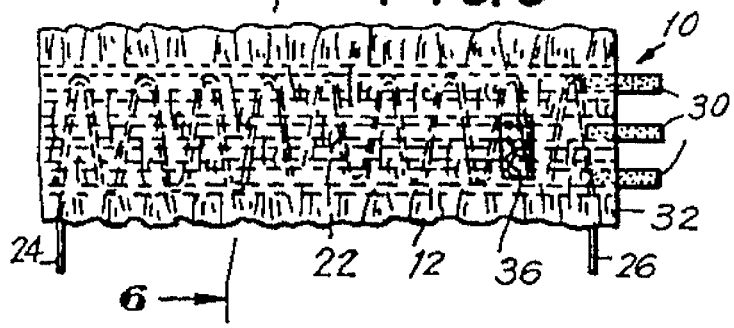
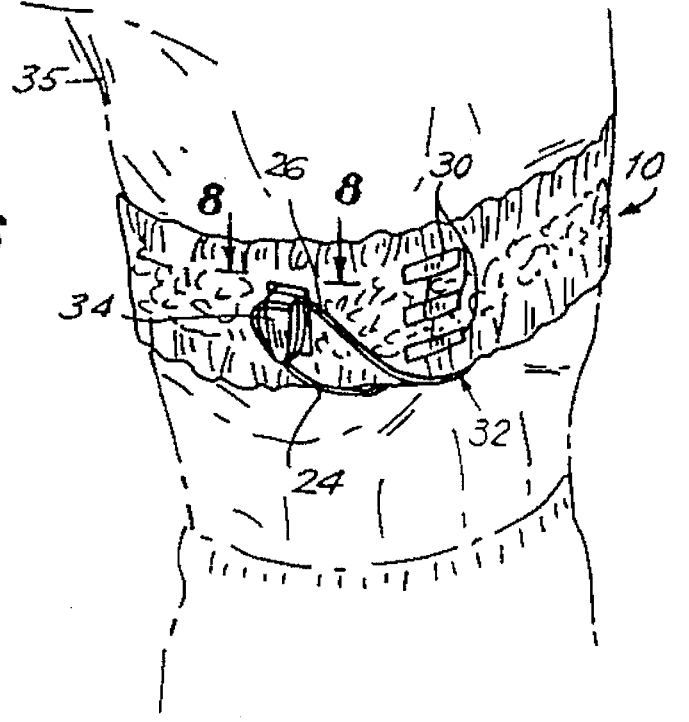

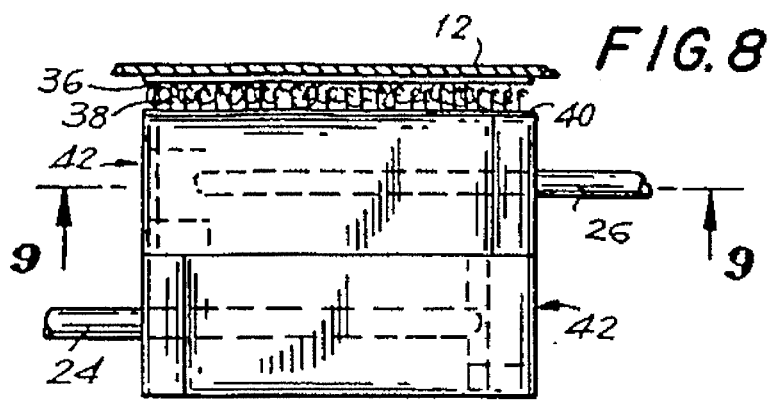
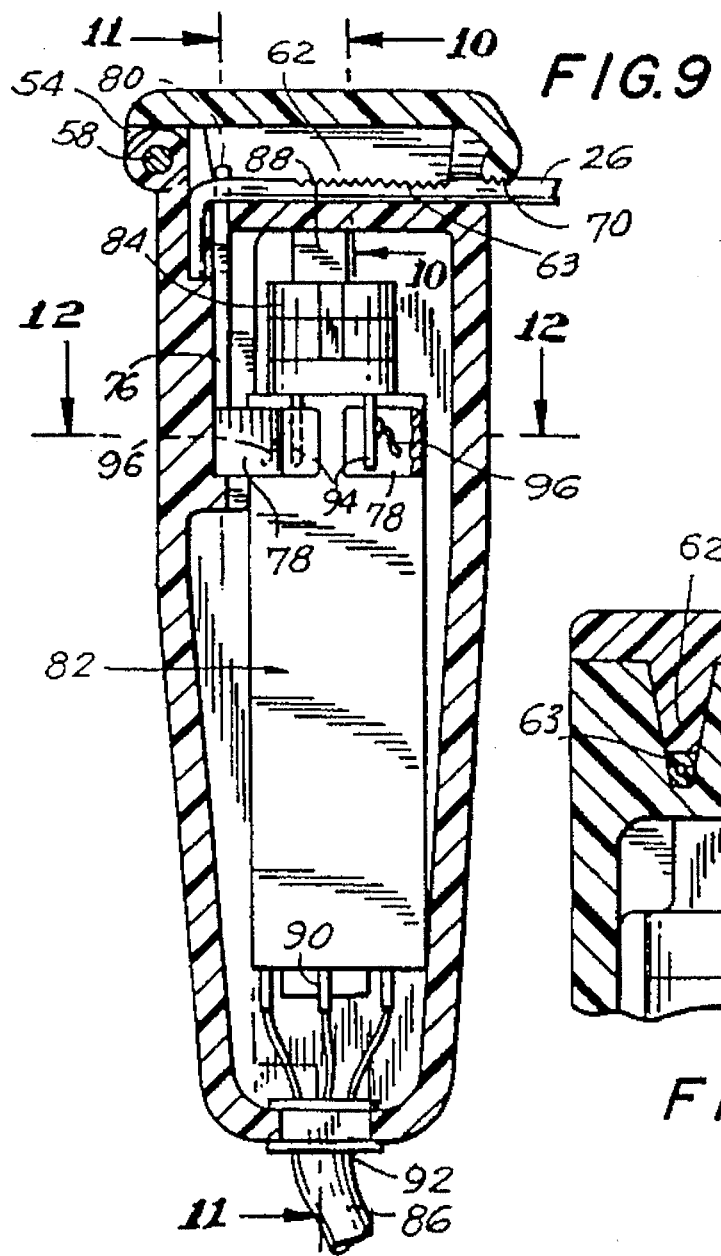
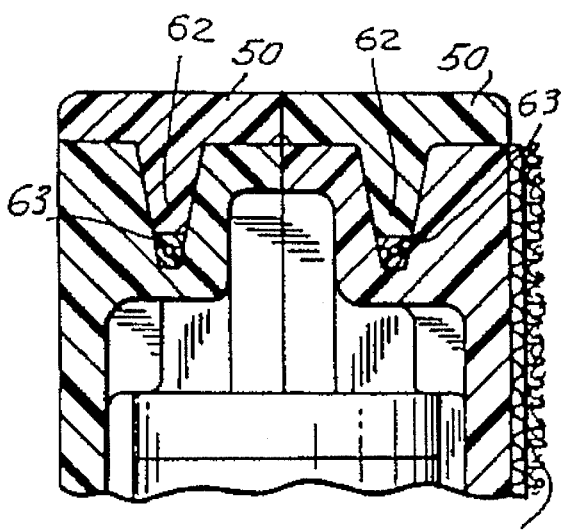

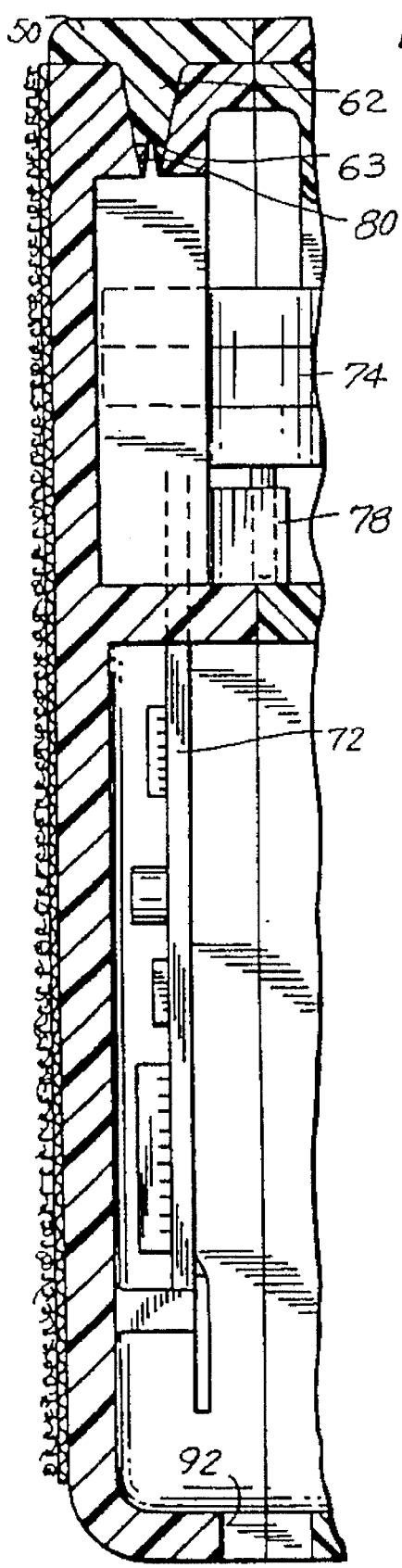
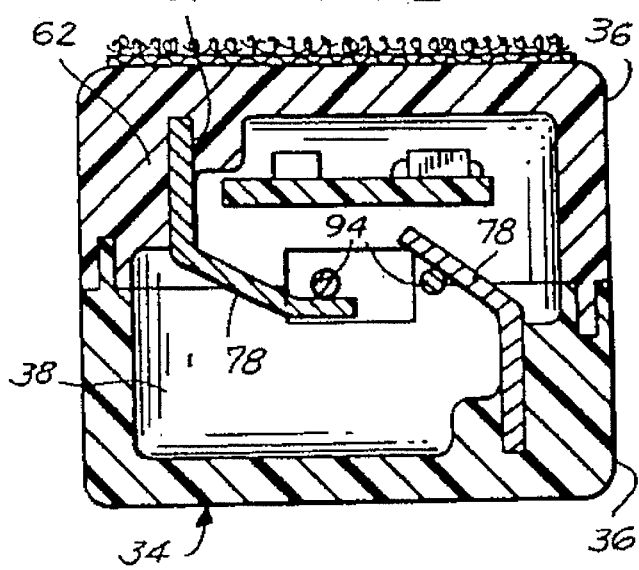

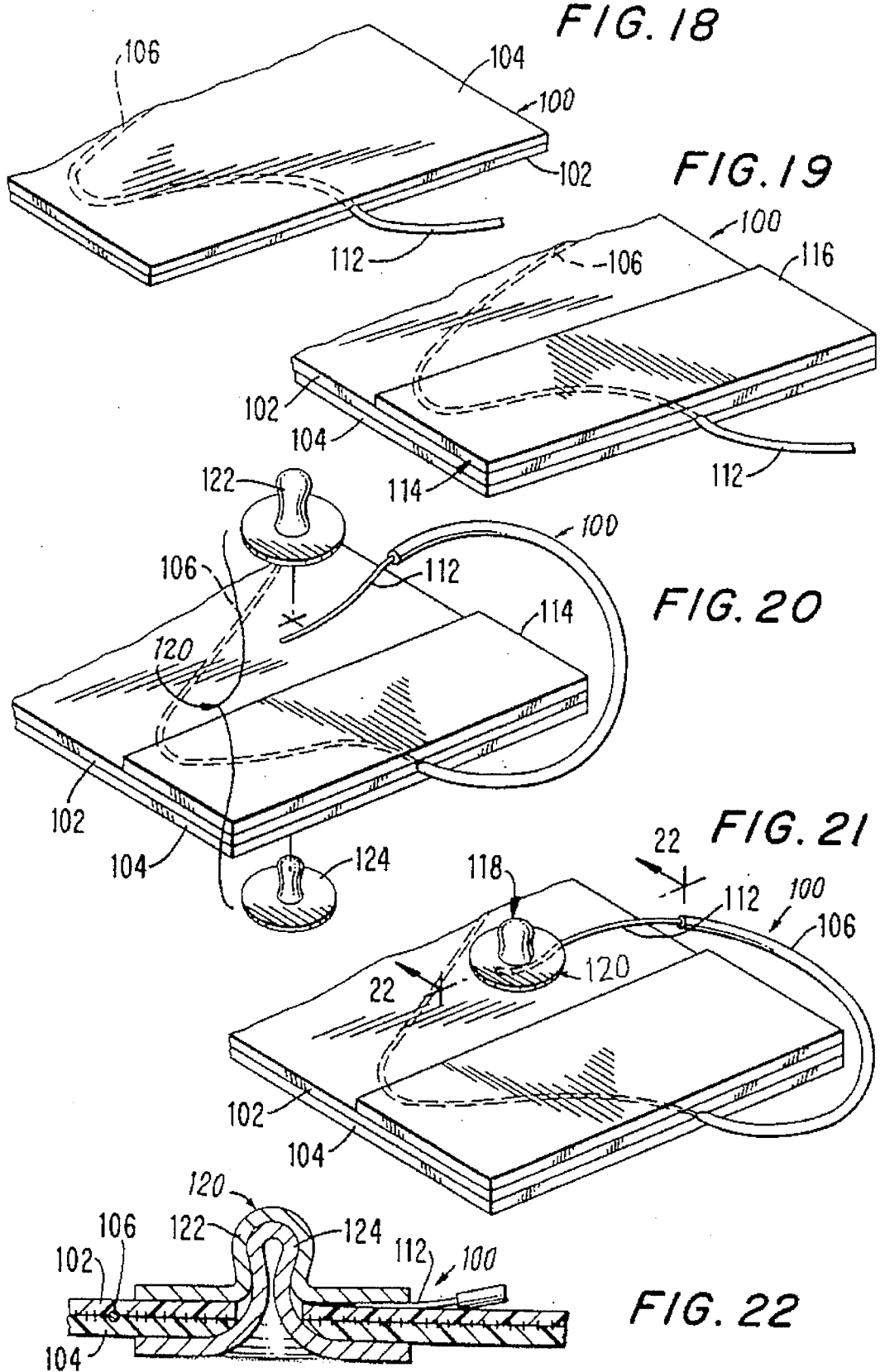

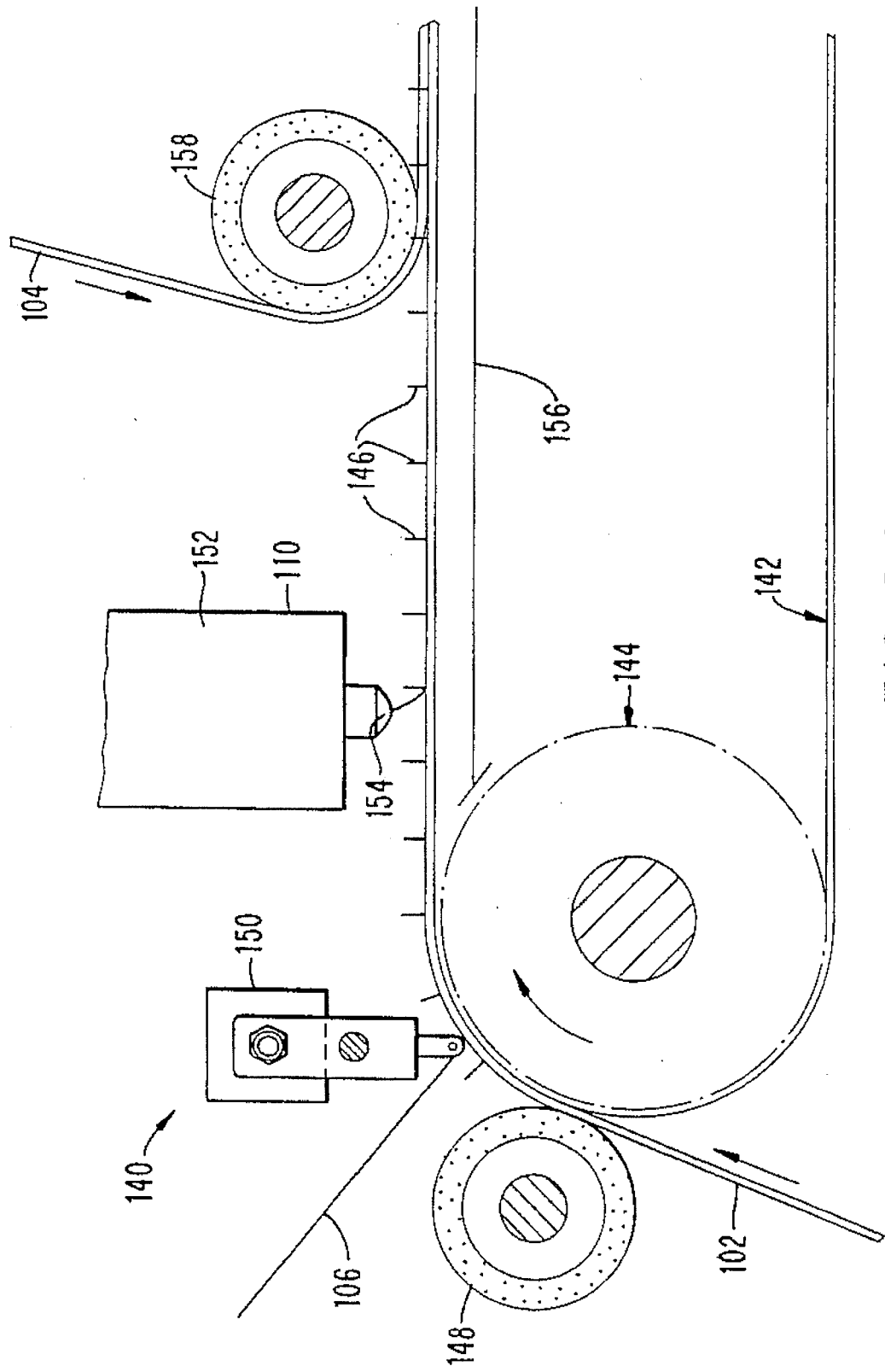

5,543,012

APPARATUS FOR MAKING A STRETCHABLE BAND-TYPE TRANSDUCER PARTICULARLY SUITED FOR USE WITH RESPIRATION MONITORING APPARATUS

This is a division of application Ser. No. 07/912,218, filed Jul. 10, 1992, abandoned, which was a continuation of application Ser. No. 07/824,752 filed Jan. 17, 1992, abandoned, which was a continuation of application Ser. No. 07/517,438 filed May 1, 1990, abandoned, which was a continuation of application Ser. No. 07/316,996 filed Feb. 28, 1989, abandoned, which was a continuation of application Ser. No. 06/932,724 filed Nov. 19, 1986, now U.S. Pat. No. 4,807,640 issued on Feb. 28, 1989.

BACKGROUND OF THE INVENTION

1. Technical Field

This invention pertains to apparatus for monitoring respiration and more particularly to apparatus of this type which employ conductors disposed about the torso of a subject for expansion and contraction therewith as the subject breathes.

2. Prior Art

Commonly assigned U.S. Pat. No. 4,308,872 entitled METHOD AND APPARATUS FOR MONITORING RESPIRATION, the contents of which are incorporated herein by reference, discloses a particular respiration monitoring apparatus. The apparatus disclosed in the patent employs two electrical conductors, e.g. wires, one disposed in encircling relation about the chest and the other disposed in encircling relation about the abdomen. Each conductor comprises the inductance element of an LC oscillator circuit of fixed capacitance. Consequently, the frequency of each oscillator varies solely in response to changes in the inductance of its respective conductor which, in turn, varies in response to changes in the volume encircled by the conductor. Therefore, as the subject breathes, the frequency changes at the outputs of the oscillators continuously indicate the extent of the expansion and contraction of the subject's chest and abdomen. As more fully explained in said U.S. Pat. No. 4,308,872, by properly processing these signals, significant respiration data may be obtained.

For the aforementioned apparatus to function properly, it is important that the conductors fit snugly about the subject's torso such that the expansions and contractions of the conductors closely follow the expansions and contractions of the chest and abdomen. Further, since it is impractical to render the conductors expandable, some other mechanism for accommodating expansion and contraction of the conductors must be employed.

In accordance with a structure now in use by applicants, each conductor is supported on a strip of woven fabric securable about the subject's torso. The fabric strip or band is stitched under tension by a plurality of longitudinally extending elastic stitches in a process known as shirring. Consequently, when the tension is released, the fabric becomes bunched or puckered along its entire length. Thereafter, an insulated wire conductor is stitched to one side of the fabric in a zigzag or saw tooth pattern. In this construction, stretching of the fabric in a longitudinal direction is accommodated by the puckers or folds with corresponding extension of the wire being accommodated by a widening and flattening of the saw tooth pattern. Consequently, by selecting the length of the band in its unstretched condition to be less than the circumference of the torso portion to be encircled, the band may be stretched about the torso portion for a snug fit. In the band structure now being described, the ends of the band are secured together as by a hook and loop type fastener, such as Velcro™, complementary portions of which are secured by stitching to either end of the band.

To accommodate connection of the wire to the balance of the oscillator circuit, the wire is secured to the fabric such that both ends of the wire terminate at the same longitudinal edge of the band at either end thereof, whereby when the band is secured about the torso, the ends of the wire are next to each other. The ends of the wire are stripped and soldered to connecting pins which are then secured in shrink tubing such that the tips of the connecting pins are exposed. The shrink tubing is stapled to the ends of the band.

The balance of the oscillator circuit is secured in a housing which, in use, may be taped to the band for the sake of convenience. A cable extending from the housing has female connectors which releasably mate with the connecting pins on the wire for completing the oscillator circuit. A second cable extends from the housing for inputting the variable output of the oscillator to additional processing circuitry as more fully described in said U.S. Pat. No. 4,308,872.

While the foregoing construction serves its intended function, it suffers from several drawbacks. One drawback is that the construction of the band is not suitable for mass production thereby adding significantly to the cost of each band. For example, the required multiple stitching operations are time consuming as is the soldering of the pins to the ends of the wire. A further drawback resides in the press fit connectors which releasably join the wire conductor to the cable extending from the oscillator housing. These connectors may become loosened due, for example, to undesirable movements of the subject, as is common in neonatal applications. A loose connector can create noise sufficient to significantly impair the quality of the transmitted signal. Even worse, the connectors may disconnect altogether. Then too, because of the low noise requirement, low noise, high cost connectors must be employed which further add to the overall cost of the band.

Another drawback, related to the first, is that owing to the high cost of the bands, it is impractical to discard them after a single use. Yet in the medical field, where sanitary considerations are paramount for sound medical reasons as well as psychological ones, it is preferred to render disposable any apparatus that comes into contact with the patient, such as occurs with the band.

Yet a further drawback is that due to the particular structure of the bands, they are not suited to cleaning by machine, as there is a risk of damaging the pins or severing the stitching securing the wire in place. Then too, the hook and loop type fastener which secures the ends of the band in encircling relation about the torso is also not suited to machine washing as it can become entangled in the fabric.

It is accordingly an object of the present invention to provide a band which overcomes the aforementioned drawbacks.

It is a further object of the present invention to provide a band which can be constructed at a sufficiently minimal cost that the band can be discarded after a single use.

It is yet a further object of the invention to provide a band which can be mass produced.

It is still a further object of the present invention to provide a band in combination with an improved housing for the oscillator circuit wherein the wire is joined to the circuitry within the housing in a manner that significantly reduces, if not eliminates, the possibility of the wire becoming loose or disconnected.

It is also an object of the invention to provide a band which does not require high cost connectors for joining the wire to the circuitry within the housing.

It is-also an object of the invention to provide a method of making a band which meets the stated objectives.

DISCLOSURE OF THE INVENTION

To meet the foregoing objects, the band of the present invention, in a broad sense, comprises a first piece of material, such as nonwoven fabric; a second piece of material, such as tissue paper; means for securing one surface of the second piece of material to one surface of the first piece of material; a piece of elastic material; means for adhesively securing the elastic material between the first and second pieces of material along a substantial portion of the length thereof with the elastic material in a stretched condition when the first and second pieces of material are in a flat condition, the first and second pieces of material defining crosswise puckers when the elastic material is in an unstretched condition for accommodating stretching of the band when the elastic material is stretched; a conductor; and means for adhesively securing the conductor between the first and second pieces of material with the conductor extending substantially the length of the band and enclosing a larger circumference upon stretching of the band.

The band of the invention is quite inexpensive as compared with prior art bands, thus making it feasible to dispose of the band after a single use. The present invention also comprises a method of making the band which further reduces the cost of the band, as the method in accordance with the present invention is suited to mass production techniques. In a broad sense, the method for making the band comprises providing a first piece of material in a flat condition, providing a second piece of material in a flat condition, stretching a piece of elastic material, securing the piece of elastic material in its stretched condition to one surface of one of the pieces of material, securing an electrical conductor to one surface of one of the pieces of material, securing the second piece of material in overlying relation with the first piece of material with the elastic material and the conductor sandwiched between the two pieces of material, and then releasing the elastic material from its stretched condition.

In a less preferred band and method of making same in accordance with the invention, one of the two pieces of material, preferably the outer piece, is not used.

The invention also comprises an enclosure specially designed for housing the components of the oscillator circuit other than the conductor incorporated in the band. The enclosure is particularly advantageous insofar as it both simplies and enhances the securement of the end portions of the conductor to the circuitry within the enclosure, thereby avoiding the need for expensive connectors while at the same time minimizing the possibility of noise caused by loosened connectors. In a broad sense, the enclosure in accordance with the present invention comprises a housing having a main body defining a chamber and first and second cap members pivotally secured to the main body for movement between an open position wherein the cap members are pivoted away from the main body and a closed position wherein the cap members contact the main body, the portion of the main body confronting the cap members in their closed positions defining first and second recesses and first and second apertures for communicating the recesses with the chamber; means secured to the housing for supporting in the chamber the components of the oscillator circuit other than the conductor; and first and second electrical contacts secured to the housing in the chamber and connected to the components of the oscillator circuit therein, one end of each contact having a point extending through one of the apertures and into the recess communicating therewith, whereby when the end portions of the conductor are disposed in the recesses and the cap members are pivoted to their closed positions for retaining the end portions in the recesses, the points pierce the end portions of the conductor for establishing electrical communication between the conductor and the other components of the oscillator circuit.

Further features and advantages of the present invention will become more fully apparent from the following detailed description and the annexed drawings of the presently preferred embodiment thereof.

BRIEF DESCRIPTION OF THE DRAWINGS

In the drawings:

FIG. 1 is a top view showing a first step in the manufacture of a band in accordance with the present invention;

FIG. 2 is a view similar to FIG. 1 showing a second step in the manufacture of a band in accordance with the present invention;

FIG. 3 is another view similar to FIG. 1 showing a third step in the manufacture of a band in accordance with the present invention;

FIG. 4 is yet another view similar to FIG. 1 showing a fourth step in the manufacture of a band in accordance with the present invention;

FIG. 5 is still a further view similar to FIG. 1 showing a fully manufactured band;

FIG. 6 is a sectional view taken substantially along lines 6—6 in FIG. 5;

FIG. 7 is a perspective view showing the band of FIG. 5 secured about a human torso, and also showing an enclosure in accordance with the present invention releasably secured to the band;

FIG. 8 is a view taken substantially along the lines 8—8 in FIG. 7;

FIG. 9 is a view taken substantially along the lines 9—9 in FIG. 8;

FIG. 10 is a view taken substantially along the lines 10—10 in FIG. 9;

FIG. 11 is a view taken substantially along the lines 11—11 in FIG. 9;

FIG. 12 is a view taken substantially along the lines 12—12 in FIG. 9;

FIG. 18 is fragmentary perspective view of a portion of the modified band;

FIG. 19 is a perspective view similar to FIG. 18 and showing an additional step in the manufacture of the modified band;

FIG. 20 is a another view similar to FIG. 18 showing a further step in the manufacture of the modified band;

FIG. 21 is still another view similar to FIG. 18 showing yet a further step in the manufacture of the modified band;

FIG. 22 is a sectional view taken substantially along the lines 22—22 in FIG. 21;

FIG. 24 is a diagrammatic view showing a machine for manufacturing the modified band,

DETAILED DESCRIPTION OF THE PREFERRED EMBODIMENT

Figure 13:
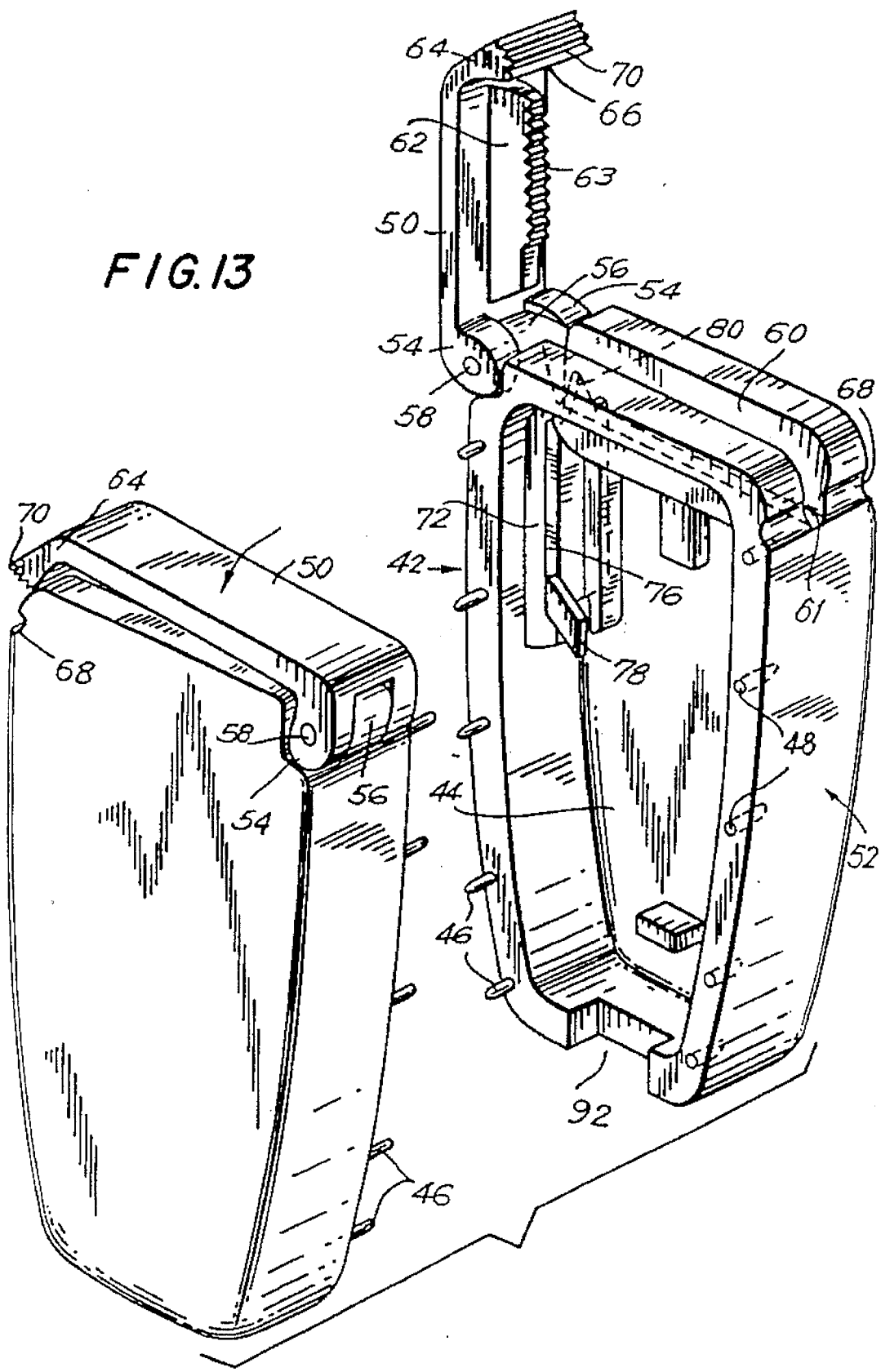
FIG. 13 is an exploded, perspective view of the enclosure in accordance with the present invention.

The disposable band in accordance with the present invention is generally designated in FIGS. 5–7 by the reference numeral 10. With reference initially to FIGS. 1–4, construction of the disposable band 10 will now be described.

In FIG. 1, a rectangular piece of non-woven fabric 12 is retained in a flat, smooth condition as by a vacuum table or other suitable device. While it is presently contemplated that any suitable non-woven fabric may be employed, presently a synthetic non-woven fabric of a type commonly used in disposable diapers, caps, surgical gowns, etc. is preferred. The dimensions of the piece of non-woven fabric 12 will, of course, vary depending on the size of the torso to be encircled by the band, and it is contemplated that bands will be made in a variety of sizes. Typically, the length of the fabric 12 will be from about eighteen inches to about sixty-four inches, and its width will be about four inches.

Referring now to FIG. 2, with the strip of non-woven fabric 12 retained in a flat, smooth condition, a plurality of longitudinally extending lines of glue 16, such as a pressure sensitive adhesive, are applied to the exposed surface 18 of the fabric 12. While the number of lines of glue may vary, it is presently contemplated that six lines of glue will be applied. The lines of glue may be applied manually or, more preferably, by a plurality of glue heads (not shown) simultaneously passing over the surface 18.

Still referring to FIG. 2, after the lines of glue 16 have been applied to the surface 18, a strip of elastic material 20, retained under tension by a jig diagrammatically represented at 14, is laid over each line of glue 16. While any suitable elastic material may be employed, natural latex is presently preferred. While the elastic strips 20 may be stretched to any suitable elongation by the jig 14, it is presently contemplated that they will be stretched to about two to three times their natural length. For purposes of illustration the elastic strips 20 are shown in FIG. 2 as extending only over the right half of the fabric 12, and it should be understood that in fact the elastic strips extend over the entire length of the glue lines 16, i.e. from one end of the non-woven fabric 12 to the other. For reasons that will be apparent hereinafter, the lines of glue 16 are sufficiently thick such that when the elastic strips 20 are applied thereon, some of the glue flows around the edges of the strips 20. While the strips 20 may be applied manually, it is contemplated that they will be positioned by machine.

Referring now to FIG. 3, with the glue 16 still in an adhesive state, and with the elastic strips 20 still retained under tension in the jig 14, a length of insulated wire 22 is applied on top of the elastic strips 20 in a zigzag pattern. For example, the wire nay be no. 30 wire comprised of three strands of no. 48 and the zigzag pattern may comprise a ninety degree saw tooth pattern. While the wire may be manually applied, it is presently contemplated that it too will be applied by machine. The wire 22 is adhesively bonded to the fabric 12 by the glue that has escaped around the edges of the elastic strips 20, but it will be appreciated that even at this stage of the manufacturing process there is still substantial glue that is not covered by the elastic strips 20 or by the wire 22. The length of the wire 22 is selected such that when it is applied as shown in FIG. 3, the end portions 24, 26 thereof extend downwardly slightly beyond the lower edge of the fabric 12 at either end thereof.

Referring now to FIG. 4, with the elastic strips 20 still retained under tension in the jig 14, a piece of tissue paper 28 or other suitable material of substantially the same size as the fabric 12 is laid on top of the fabric 12 so as to cover the elastic bands 20 and wire 22. The tissue paper 28 is secured to the fabric 12 by the remaining exposed glue on the surface 18.

With the elastic strips 20 retained in a stretched condition and with the fabric 12 and tissue paper 28 in a flat condition on either side thereof, the entire assembly is pressed together, as between a pair of rollers, for strengthening the adhesive bond between the fabric 12, the elastic strips 20, the wire 22 and the tissue paper 28. The elastic strips 20 are then released from the jig whereupon the edges of the elastic strips are trimmed to be coincident with the edges of fabric 12 and tissue paper 28.

When the ends of the elastic strips 20 are released from the jig 14, it will be apparent that the elastic strips return to an unstretched condition. Referring to FIG. 5, return of the elastic strips 20 to their unstretched condition results in puckering or gathering of the fabric 12 and tissue paper 28 as well as a contraction of the wire, the latter being manifested by a saw tooth of shorter period, i.e. a taller and narrower zigzag pattern.

Next, a plurality of strips of tape, shown by way of example in FIG. 5 as three strips of tape 30, are secured to one vertical edge 32 of the assembly. For example, the adhesive strips 30 may comprise peel and stick tabs of a type commonly found on diapers. As shown, one end of each peel and stick tab 30 is adhesively secured at the edge 32, with the other end of the tab extending beyond the edge. The portion of the tab 30 extending beyond the edge 32 comprises an adhesive surface covered by a removable strip of paper or the like. This arrangement is ideal for the present invention as the adhesive on the tabs 30 remains covered for ease of handling until the band 10 is used.

FIG. 7 illustrates the band 10 secured about the torso of a subject 35. While only one band 10 is illustrated in FIG. 7, typically two bands will be employed, one secured about the chest of the subject 35 and the other secured about the abdomen. As it is important that the wire 22 fit snugly against the subject 35 for expansion and contraction as the subject breathes, each band is preselected to be shorter than the circumference of the torso portions to be encircled. To secure the band 10 about the subject 35, the band is placed against the torso of the subject 35 with the fabric side contacting the subject. The band 10 is stretched by pulling at the ends thereof until the two ends of the band are in confronting relation. As will be apparent from the foregoing description, stretching of the band 10 is accommodated by the elastic strips 22 and by the puckers in the fabric 12 and tissue paper 28, which gradually return to a smooth, unpuckered condition as the band is stretched. The wire 22, being adhesively secured to the fabric 12, elastic strips 20 and tissue paper 28, expands in the longitudinal direction as the band 10 is stretched, expansion of the wire 22 being manifested by a wider and flatter sawtooth configuration than that illustrated in FIG. 5.

With the ends of the band 10 in confronting relation, the paper covering the adhesive on the tabs 30 is peeled away, whereupon the tabs are attached to the confronting end of the band, thereby securing the band 10 about the torso of the subject 35. It will be appreciated that with the band 10 thus secured, the band 10 is free to expand and contract as the subject breathes.

As described above, and as is explained in detail in commonly owned U.S. Pat. No. 4,308,702, the wire 22 in the band 10 comprises the inductance component of an LC oscillator circuit. Referring to FIG. 7, the balance of the LC oscillator circuit is incorporated in a housing 34 secured to the band 10. Because the components in the housing 34 are relatively expensive, the housing 34 is removably secured to the band 10 to accommodate repeated use. For this purpose now referring to FIG. 8, a patch 36 of a hook and loop type fastener, such as velcro™, is secured, as by an adhesive, to the tissue paper side of the band 10, preferably near the edge 32, and a complementary patch 38 is secured, also as by an adhesive, to the back wall 40 of the housing 34. The housing may then be removably secured to the band 10 by contacting patch 38 with patch 36.

To complete the LC oscillator circuit comprising the wire 22 and the circuitry within the housing 34, the end portions 24, 26 of the wire 22 must be connected to the circuitry within the housing. The housing 34 is especially designed to accomplish this objective without requiring any special pins or connectors on the end portions 24, 26 of the wire 22. The housing 34 will now be described in greater detail with particular reference to FIGS. 8–13.

Housing 34 comprises identical halves 42 disposed in confronting relation for defining a chamber 44 within the housing. The two halves 42 are secured together as by an adhesive with registry between the halves 42 being assured by pins 46 and corresponding holes 48 along the confronting faces of the halves 42. As each half 42 is identical, only one will be described in detail below.

Each half 42 comprises a cap member 50 pivotally secured to a main body 52, both of which are preferably comprised of plastic, such as polyvinylchloride. To effect pivotal securement, the cap 50 has a pair of spaced feet 54 disposed on either side of a cylinder 56 formed at an upper corner of the body 52. A pin 58 extending through aligned apertures in the feet 54 and cylinder 56 secures cap 50 to body 52 for pivotal movement relative thereto.

As best shown in FIGS. 10 through 13, a V-shaped groove 60 extends across the top of each body 52. The groove 60 receives a complementary shaped projection 62 depending from the cap 50 when the cap is pivoted closed. Referring to FIG. 13, a bore 61 in the vertical sidewall of the body 52 nearest the cylinder 56 extends through the bottom defining wall of the recess 60 such that the bore communicates with the recess. For reasons that will be explained below, and as shown, a portion of the edge 63 of the projection 62 is serrated.

The free end 64 of each cap 50 has an inwardly extending ridge 66 which seats in a complementary recess 68 in the sidewall of the body 52, the edge 66 and recess 68 providing a detent for releasably securing the cap 50 in the closed position. As shown, the free end 64 of the cap 50 is knurled as at 70 to facilitate pivotal movement of the cap 50.

A boss 72 having a vertically extending recess 74 is provided on the interior sidewall of each body 52 beneath the cylinder 56. As shown, an electrical contact 76 seats in the recess 74. The lower end of the contact 76 has an arm 78 extending into the chamber 44 for reasons that will explained below. The upper end of the contact 76 tapers to a sharp point 80 which extends through an aperture in the bottom defining wall of the recess 60 such that the point 80 extends into the recess.

The balance of the oscillator circuit secured within the housing 34 is diagrammatically illustrated in FIGS. 9, 11 and 12 by a circuit board 82, shown in FIG. 9, and a coupling transformer 84, the primary leads of the transformer 84 being soldered to the circuit board 82. As shown, a three wire cable 86 is soldered to the end of the board 82 opposite the transformer 84. Cable 86 may be about six feet in length and terminate in a standard telephone type connector which, directly or through an extension cable, may be secured to respiration monitoring apparatus of the type described in said U.S. Pat. No. 4,308,872.

To assemble the housing 34, the circuit board 82 and attached transformer 84 are seated inside one half 42 of the housing 34. Proper positioning of the board 82 and transformer 84 is assured by bosses 88 and 90 formed on the inside backwall of the body 52. As shown, the cable 86 is laid into a cut out 92 formed in the lower end of the body 52.

Adhesive is next applied to the pins 46 on the housing halves 42, whereupon the two halves are brought into contact along upon one vertical edge. With the other edges of the housing halves 42 held in spaced apart relation, the secondary leads 94 on the transformer 84 are soldered to the arms 78 of the contacts 76 via two short wires 96 extending from the leads 94. At this point, the spaced apart edges of the housing halves 42 are brought into contact, thereby closing the housing 34.

The housing 34, with the caps 50 open, is now brought into proximity with the end portions 24, 26 of the wire 22. One end of the wire is placed in the bore 61 in one half 42 of the housing 34, and the other end of the wire is placed in the other bore 61 in the other half 42 of the housing 34. Thereafter, the end portions 24, 26 of the wire 22 are laid in the recesses 60 in their respective housing halves 42. At this point, the caps 50 are pivoted to the closed position, whereupon the unserrated portions of the edges 63 of the projections 62 force the wire end portions 24, 26 against the pins 80 with sufficient force that the pins 80 pierce the wire insulation and make contact with the conductor inside. When the caps are fully closed, as confirmed by snapping of the ridges 66 in the recesses 68, the wire end portions 24, 26 are retained firmly in place in the recesses 60 by the serrated portions of the edges 63. It will be appreciated that by thus connecting the secondary leads 94 of the transformer 84 to the end portions 24, 26 of the wire 22 via the contacts 76, the LC oscillator circuit is completed and is available for connection to appropriate processing circuitry via the cable 86. At this point, the housing 34 may be secured to the band 10 by pressing the patch 38 on the backwall 40 of the housing 34 against the complementary patch 36 on the band 10.

When use of the band is completed, the caps 50 are pivoted to their open positions, whereupon the wire end portions 24, 26 may be removed from the housing 34. At this point or before, the housing 34 may be separated from the band 10 by pulling the patch 38 away from the patch 36. The band 10, owing to its inexpensive structure, may then be discarded. The housing 34 containing the balance of the oscillator circuit may be retained for repeated use. As described above, typically two bands 10 are used with each subject, with one housing 34 being secured to each band.

In a modified band construction in accordance with the invention, either the fabric 12 or tissue paper 28, preferably tissue paper 28, is dispensed with. When this embodiment is employed, it will be apparent that the adhesive must cure before the band is available for use. Accordingly, to insure curing of the adhesive, an adhesive having a controllable cure time, such as a thermosetting adhesive, is preferred for this embodiment. While this embodiment is less preferred as it leaves the conductor exposed on one side, it does have the advantage of reduced cost as it eliminates one of the two pieces of material.

Referring now to FIGS. 14–24, a modified disposable band in accordance with the present invention is generally designated by the reference numeral 100. As best seen in FIGS. 17 through 22, the band 100 includes two rectangular strips 102, 104 of elastic material, such as am open cell polyester foam, having a conductor 106 sandwiched therebetween. While an open cell polyester foam is preferred for the strips 102, 104, a closed cell foam could also serve, as could other types of foams, such as polyurethane foams or, for that matter, other types of elastic material, such as Spandex TM. The advantage of using a foam is that it is extremely inexpensive, enjoys natural elasticity, and has a high coefficient of fiction, which prevents slippage once the band is placed on the subject's torso.

Figure 14:
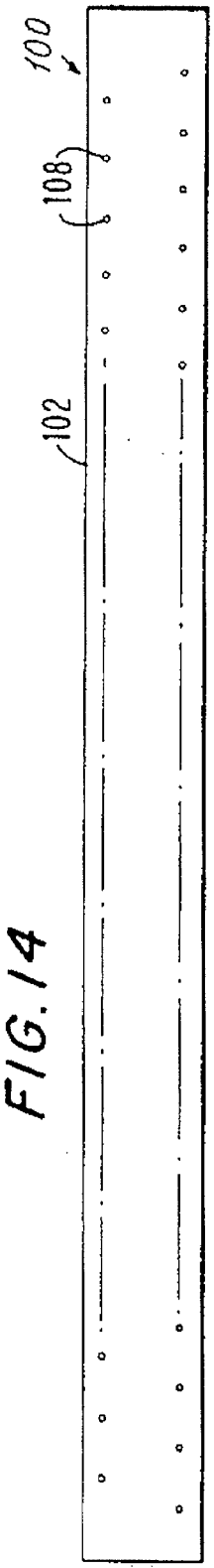
FIG. 14 is a top view showing a first step in the manufacture of a modified band in accordance with the present invention.
Figure 15:
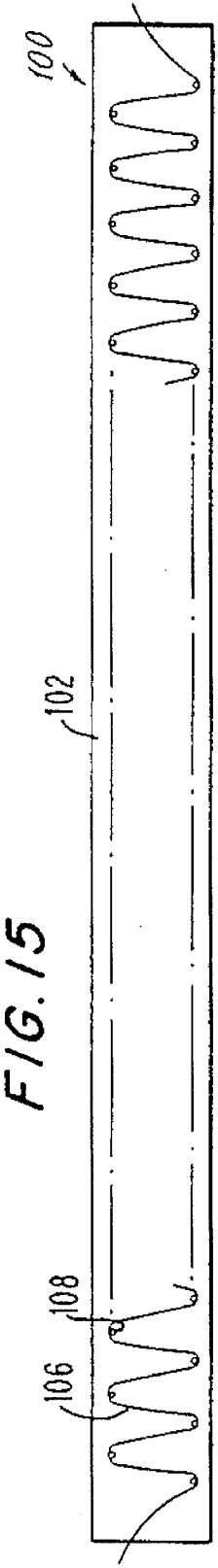
FIG. 15 is a view similar to FIG. 14 showing a second step in the manufacture of the band of FIG. 14.

To assemble the band 100, and referring in initially to FIG. 14, one strip of the polyester foam 102 is laid flat whereupon staggered pins 108 are stuck into the strip 102 along both longitudinal edges. Next, and as shown in FIG. 15, the conductor 106 is laid on top of the strip 102 in a zig zag pattern using the pins 108 as guides to hold the conductor in place. As with the band 10, the conductor may comprise insulated no. 30 wire comprised of 3 strands of no. 48 and the zig zag pattern may comprise a 90 degree saw tooth pattern. As shown, a sufficient length of wire 106 is used such that the free ends of the wire extend beyond the strip 102. The reason for this will be explained below.

Figure 16:
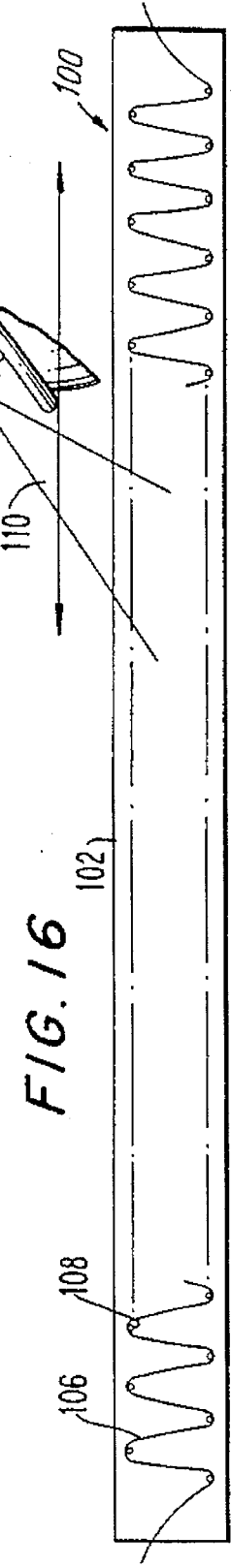
FIG. 16 is another view similar to FIG. 14 showing a third step in the manufacture of the band of FIG. 14.
Figure 17:
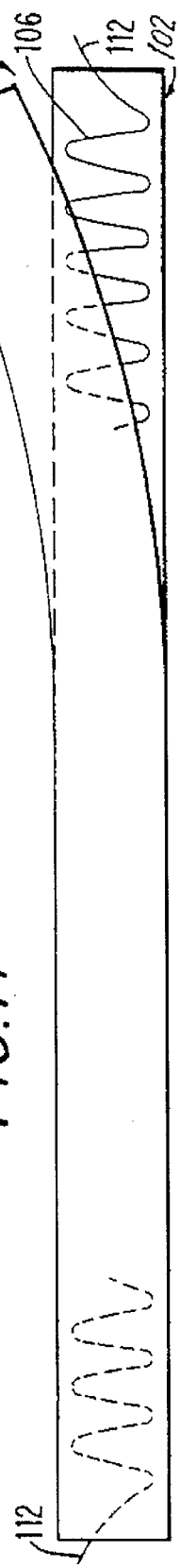
FIG. 17 is yet another view similar to FIG. 14 showing a fourth step in the manufacture of the band of FIG. 14.

Referring now to FIG. 16, once the conductor 106 is laid on the strip 102, the side of the strip on which the conductor is applied is covered with an adhesive. For example, a hot melt adhesive 110 may be sprayed on. Thereafter, and as shown in FIG. 17, the second strip 104 of polyester foam, which is of the same dimensions as the first strip 102, is applied to the assembly comprising strip 102 and conductor 106 such that the conductor 106 is sandwiched between the strips 102 and 104. When this is done, the adhesive 110 serves both to secure the strips 102 and 104 together and also to secure the conductor 106 to the strips 102 and 104. With the strips 102, 104 and conductor 106 thus assembled, the free ends of the conductor 106 extend beyond the strips 102, 104 at opposite ends of the band 100 (FIG. 18).

At this point, and as best seen in FIG. 19, a strip of double sided adhesive 114 is secured at one end of the band 100. In a well known manner, the exposed side of the adhesive strip 114 is covered with a strip of paper 116 which may be peeled away for exposing the adhesive therebeneath for reasons explained below.

Referring now to FIGS. 20–22 the free ends 112 of the conductor 106 are stripped of insulating material whereupon they are secured in electrical conducting relation to the male portions 118 of electrically conducting snap fasteners 120. While only one such male snap fastener portion 118 is shown in FIGS. 20–22, it will be appreciated that there is one male portion 118 at each end of the band 100 (see FIG. 23). As shown, each male snap fastener portion 118 comprises a front 122 and a back 124. The front 122 and back 124 are placed on either side of the sandwich comprising strips 102, 104 and conductor 106 and then squeezed together in a well known manner for securing the male portion 118 to said sandwich. During this squeezing operation, the proximal stripped end 112 of the conductor 106 is placed between the front 122 and back 124 such that as the male portion 118 is assembled, the free end of the conductor 106 is secured therebetween in electrical conducting relation therewith. As an additional measure, the free end of the conductor 112 may be soldered to the front 122 or back 124 of the male snap fastener portion 118 for further insuring securement of the free end 112 of the conductor 106 thereto. Snaps 120 suitable for practicing the invention are sold, for example, by Stimpson Co., Inc., and it will be appreciated by those of ordinary skill that snaps other than those described herein may be employed.

To utilize the band 100, the band is stretched about the torso of a subject until its free ends are in confronting relation. Stretching of the band about the torso is accommodated by both the elasticity of the strips 102, 104 and the zig zag pattern of the conductor sandwiched therebetween. In a manner more fully described above in connection with the band 10, during stretching the zig zag pattern of the conductor 106 flattens out.

Figure 23:
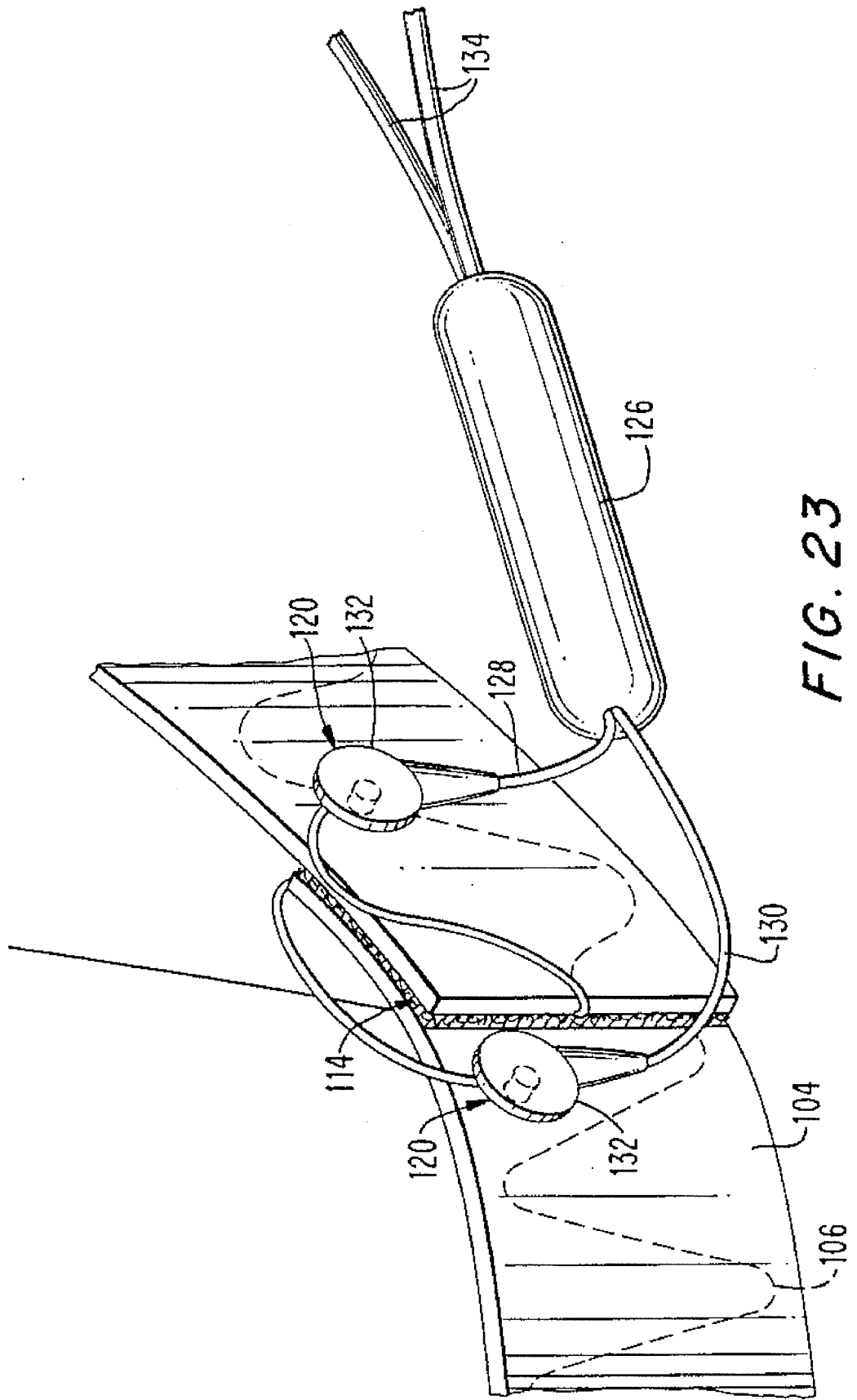
FIG. 23 is perspective view showing the modified band in use.

Once the free ends of the band 100 are in confronting relation, the paper cover 116 on the adhesive strip 114 is peeled away, whereupon the other end of the band 100 is secured to the adhesive strip thereby securing the free ends of the band together. At this point, all that remains is to secure the oscillator electronics to the ends of the conductor 106. As best seen in FIG. 23, the electronics are mounted in a cylindrical plastic housing 126 having wire leads 128, 130 each terminating in an electrically conductive female snap fastener portion 132. It will be apparent that when the female snap fastener portions 132 are secured to the male snap fastener portions 118, electrical conducting contact will be established between the wire leads 128, 130 and the ends of the conductor 106. As explained above for the band 10, the wires 134 extending from the other end of the housing 126 may be connected to a respiration monitoring apparatus of the type disclosed in U.S. Pat. No. 4,308,872.

The foregoing description assumes manual assembly of the band 100. It will be appreciated, however, that production quantities require mass assembly. Accordingly, and referring now to FIG. 24, a machine 140 for manufacturing bands 100 is diagrammatically illustrated. As shown, the machine 140 employs an endless belt 142 extending about a pair of pulleys 144, only one of which is shown in FIG. 24, and only one of which is driven. The endless belt 142 has a plurality of pins 146 protruding therefrom, the pins being arranged in the same spaced, staggered fashion described above in connection with FIG. 14.

The bottom strip 102 of foam is fed from a feed roll (not shown) onto the endless belt 142. The compression roll 148 presses the strip 102 onto the endless belt 142 until the pins 146 extend therethrough. Next, a shuttle 150 applies the wire 106 to the strip 102 in the required zig zag pattern about the pins 146. Such that the pins hold the wire in place until the adhesive is applied.

Thereafter, the strip 102 with the conductor 106 thereon passes under a bin 152 containing the adhesive 110 which is applied to the strip 102 via a nozzle 154 at the bottom of the bin. As shown, in the stretch between the two pulleys 144, the endless belt 142 is supported against downward motion by a belt support 156.

Next, the upper strip of foam 104 is fed from a feed roll (not shown) about a second foam compression roll 158 which presses the strip 104 down against the strip 102 and the conductor 106. It will be apparent that during this compression, the adhesive serves to firmly secure together the sandwich comprising the strips 102, 104 and the conductor 106.

Thereafter, the completed sandwich is removed from the endless belt 142 by a take up roll (not shown). The sandwich may then be cut into appropriate lengths, whereupon the final steps may be completed manually, i.e. stripping the free ends 112 of the conductor 106, applying them between male snap fastener portions 118, and applying the adhesives strips 114.

While certain embodiments of the present invention have been described herein, it will be appreciated by those of ordinary skill in the art that still further changes and modifications may be made therein without departing from the spirit and scope of the invention. Accordingly, the above description should be construed as illustrative, and not in limiting sense, the scope of the invention being defined by the following claims.

We claim:

1. An apparatus for making a disposable band incorporating an electrical conductor disposable about a three-dimensional object for expansion and contraction therewith, comprising:

an endless belt;

a plurality of guide pins disposed on the endless belt so as to project from a surface thereof;

a first feed means for feeding a first strip of elastic material onto the surface of the endless belt from which the plurality of guide pins project;

a first pressing means for pressing the first strip of elastic material onto the surface of the endless belt from which the plurality of guide pins project so that the guide pins protrude through the first strip of elastic material;

a conductor applicator means for disposing the electrical conductor onto the first strip of elastic material after the first strip has been pressed onto the surface of the endless belt in accordance with a pattern defined by the guide pins;

a second feed means for feeding a second strip of elastic material onto the endless belt so as to sandwich the electrical conductor between the first and second strips of elastic material; and a second pressing means for pressing the second strip of elastic material onto the first strip of elastic material with the conductor between the two strips of elastic material so that the guide pins protrude through the second strip of elastic material.

2. The apparatus of claim 1, wherein the first and second pressing means each comprises a compression roll disposed adjacent the endless belt having a structure such that the guide pins on the endless belt are capable of penetrating the compression rolls to a depth of substantially a length of the guide pins.

3. The apparatus of claim 1, wherein the conductor applicator means comprises a shuttle.

4. The apparatus of claim 1, further comprising a belt support means disposed adjacent to and along a portion of the length of the endless belt.

5. The apparatus of claim 1, further comprising an adhesive applicator for applying adhesive to a surface of the first strip of elastic material to which the conductor is applied.

6. The apparatus of claim 5, wherein the adhesive applicator comprises a container having a nozzle directed toward the endless belt.

* * * * *